United States Patent
Kozloski et al.

(10) Patent No.: US 9,711,027 B2
(45) Date of Patent: Jul. 18, 2017

(54) SUGGESTING ADJUSTMENTS TO A HELMET BASED ON ANALYSIS OF PLAY

(71) Applicant: INTERNATIONAL BUSINESS MACHINES CORPORATION, Armonk, NY (US)

(72) Inventors: James R. Kozloski, New Fairfield, CT (US); Mark C. H. Lamorey, Williston, VT (US); Clifford A. Pickover, Yorktown Heights, NY (US); John J. Rice, Mohegan Lake, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 134 days.

(21) Appl. No.: 14/709,572

(22) Filed: May 12, 2015

(65) Prior Publication Data
US 2016/0331302 A1 Nov. 17, 2016

(51) Int. Cl.
| | | |
|---|---|---|
| G08B 23/00 | (2006.01) |
| G08B 21/04 | (2006.01) |
| A61B 5/00 | (2006.01) |
| A42B 3/04 | (2006.01) |
| A61B 5/11 | (2006.01) |

(52) U.S. Cl.
CPC .......... *G08B 21/0446* (2013.01); *A42B 3/046* (2013.01); *A42B 3/0433* (2013.01); *A61B 5/1114* (2013.01); *A61B 5/1121* (2013.01); *A61B 5/6803* (2013.01); *A61B 5/742* (2013.01); *A61B 5/746* (2013.01); *A61B 5/4848* (2013.01); *A61B 2503/10* (2013.01); *A61B 2562/0219* (2013.01)

(58) Field of Classification Search
CPC ....... A61B 5/486; A61B 5/6803; A61B 5/742; A61B 5/7275; A61B 5/746; A61B 2503/10; A42B 3/0453; G08B 21/0461
USPC ...................................................... 340/573.1
See application file for complete search history.

(56) References Cited

U.S. PATENT DOCUMENTS

| | | | |
|---|---|---|---|
| 6,240,571 B1 | 6/2001 | Infusino |
| 6,665,884 B1 | 12/2003 | Demps et al. |
| 6,826,509 B2 | 11/2004 | Crisco, III et al. |
| 8,621,673 B1 | 1/2014 | Pietrantonio |

(Continued)

FOREIGN PATENT DOCUMENTS

CA 2772644 A1 6/2012

OTHER PUBLICATIONS

List of IBM or Patent Applications Treated as Related—Date Filed: Aug. 6, 2015; 2 pages.

(Continued)

*Primary Examiner* — Nader Bolourchi
(74) *Attorney, Agent, or Firm* — Cantor Colburn LLP; Vazken Alexanian

(57) ABSTRACT

Embodiments include method, systems and computer program products for suggesting adjustments to an adjustable helmet based on analysis of play. Aspects include monitoring a plurality of sensors in the adjustable helmet and performing an analysis of play for a user of the adjustable helmet based on data received from the plurality of sensors. Aspects also include determining if an adjustment to the adjustable helmet should be made based on the analysis of play and creating an alert indicating that an adjustment to the helmet is needed.

11 Claims, 5 Drawing Sheets

(56) References Cited

U.S. PATENT DOCUMENTS

| | | | |
|---|---|---|---|
| 2002/0183657 A1* | 12/2002 | Socci | A61B 5/1114 600/595 |
| 2005/0067816 A1* | 3/2005 | Buckman | A41D 13/018 280/730.1 |
| 2008/0158502 A1* | 7/2008 | Becker | A61F 9/067 351/44 |
| 2010/0140241 A1* | 6/2010 | Martin | A61F 9/065 219/130.21 |
| 2011/0144539 A1 | 6/2011 | Ouchi | |
| 2011/0215931 A1* | 9/2011 | Callsen | F41H 1/04 340/573.1 |
| 2012/0124720 A1 | 5/2012 | Evans et al. | |
| 2012/0292488 A1 | 11/2012 | Saadat | |
| 2012/0297525 A1 | 11/2012 | Bain | |
| 2013/0074248 A1* | 3/2013 | Evans | G08B 21/02 2/421 |
| 2013/0312163 A1 | 11/2013 | Van Waes | |
| 2013/0340147 A1 | 12/2013 | Giles | |
| 2014/0020158 A1 | 1/2014 | Parsons et al. | |
| 2014/0173812 A1 | 6/2014 | Krueger | |
| 2015/0038874 A1 | 2/2015 | Abreu | |
| 2016/0125653 A1* | 5/2016 | Denis | B23K 9/322 348/90 |

OTHER PUBLICATIONS

U.S. Appl. No. 14/744,061, filed Jun. 19, 2015; Entitled: Monitoring A Person for Indications of a Brain Injury.

U.S. Appl. No. 14/744,063, filed Jun. 19, 2015; Entitled: Monitoring a Person for Indications of a Brain Injury.

U.S. Appl. No. 14/744,064, filed Jun. 19, 2015; Entitled: Monitoring a Person for Indications of a Brain Injury.

U.S. Appl. No. 14/745,491, filed Jun. 22, 2015; Entitled: "Automatic Adjustment of Helmet Parameters Based on a Category of Play".

U.S. Appl. No. 14/745,492, filed Jun. 22, 2015; Entitled: "Detection of a Traumatic Brain Injury with a Mobile Device".

U.S. Appl. No. 14/745,493, filed Jun. 22, 2015; Entitled: "Suggesting Adjustments to a Helmet Based on Analysis of Play".

U.S. Appl. No. 14/745,494, filed Jun. 22, 2015; Entitled: "Mouthguard for Analysis of Biomarkers for Traumatic Brain Injury".

U.S. Appl. No. 14/745,495, filed Jun. 22, 2015; Entitled: "Helmet Having an Embedded Cooling Array".

U.S. Appl. No. 14/745,497, filed Jun. 22, 2015; Entitled: "Monitoring Impacts Between Individuals for Concussion Analysis".

U.S. Appl. No. 14/745,498, filed Jun. 22, 2015; Entitled: "Helmet Having a Cumulative Concussion Indicator".

List of IBM Patents or Patent Applications Treated as Related—Date Filed: May 12, 2015; 2 pages.

U.S. Appl. No. 14/664,987, filed Mar. 23, 2015; Entitled: Monitoring a Person for Indications of a Brain Injury.

U.S. Appl. No. 14/664,989, filed Mar. 23, 2015; Entitled: Monitoring a Person for Indications of a Brain Injury.

U.S. Appl. No. 14/664,991, filed Mar. 23, 2015; Entitled: Monitoring a Person for Indications of a Brain Injury.

U.S. Appl. No. 14/709,563, filed May 12, 2015; Entitled: "Helmet Having a Cumulative Concussion Indicator".

U.S. Appl. No. 14/709,564, filed May 12, 2015; Entitled: "Monitoring Impacts Between Individuals for Concussion Analysis".

U.S. Appl. No. 14/709,568, filed May 12, 2015; Entitled: "Helmet Having an Embedded Cooling Array".

U.S. Appl. No. 14/709,570, filed May 12, 2015; Entitled: "Mouthguard for Analysis of Biomarkers for Traumatic Brain Injury".

U.S. Appl. No. 14/709,574, filed May 12, 2015; Entitled: "Automatic Adjustment of Helmet Parameters Based on a Category of Play".

U.S. Appl. No. 14/709,575, filed May 12, 2015; Entitled: "Detection of a Traumatic Brain Injury with a Mobile Device".

\* cited by examiner

SUGGESTING ADJUSTMENTS TO A HELMET BASED ON ANALYSIS OF PLAY

RELATED APPLICATIONS

This application is related to: U.S. application Ser. No. 14/709,575; Filed: May 12, 2015; U.S. application Ser. No. 14/709,574; Filed: May 12, 2015; U.S. application Ser. No. 14/709,570; Filed: May 12, 2015; U.S. application Ser. No. 14/709,563; Filed: May 12, 2015; U.S. application Ser. No. 14/709,568; Filed: May 12, 2015; U.S. application Ser. No. 14/709,564; Filed: May 12, 2015; U.S. application Ser. No. 14/664,987; Filed Mar. 23, 2015; U.S. application Ser. No. 14/664,989; Filed: Mar. 23, 2015; and U.S. application Ser. No. 14/664,991; Filed: Mar. 23, 2015; the contents of each of which are herein incorporated by reference in their entirety.

BACKGROUND

The present disclosure relates to the suggestion of adjustments to a helmet to mitigate the risk of brain injuries, and more specifically, to methods, systems and computer program products for suggesting adjustments to a helmet based on analysis of play.

Generally speaking, safety is a primary concern for both users of helmets and manufacturers of helmets. Helmets are used by individuals that participate in activities that have risk of head trauma, such as the area of sports, biking, motorcycling, etc. While helmets have traditionally been used to provide protection from blunt force trauma to the head, an increased awareness of concussion causing forces has motivated a need for advances in helmet technology to provide increased protection against concussions. A concussion is a type of traumatic brain injury that is caused by a blow to the head that shakes the brain inside the skull due to linear or rotational accelerations. Recently, research has linked concussions to a range of health problems, from depression to Alzheimer's, along with a range of brain injuries. Unlike severe traumatic brain injuries, which result in lesions or bleeding inside the brain and are detectable using standard medical imaging, a concussion is often invisible in brain tissue, and therefore only detectable by means of a cognitive change, where that change is measurable by changes to brain tissue actions, either neurophysiological or through muscle actions caused by the brain and the muscles resulting effects on the environment, for example, speech sounds.

Currently available helmets include a hard outer shell and internal padding that is designed to mitigate the risk of brain injuries. These helmets are designed to accommodate all types of impacts regardless of the probability of the occurrence of specific impacts during various types of usage.

SUMMARY

In accordance with an embodiment, a method for suggesting adjustments to a helmet based on analysis of play includes monitoring a plurality of sensors in the adjustable helmet and performing an analysis of play for a user of the adjustable helmet based on data received from the plurality of sensors. The method also includes determining if an adjustment to the adjustable helmet should be made based on the analysis of play and creating an alert indicating that an adjustment to the helmet is needed.

In accordance with another embodiment, an adjustable helmet for mitigating the risk of brain injuries includes a processor and one or more sensors is provided. The processor is configured to perform a method that includes monitoring the one or more sensors in the adjustable helmet and performing an analysis of play for a user of the adjustable helmet based on data received from the one or more sensors. The method also includes determining if an adjustment to the adjustable helmet should be made based on the analysis of play and creating an alert indicating that an adjustment to the helmet is needed.

In accordance with a further embodiment, a computer program product for suggesting adjustments to a helmet based on analysis of play includes a non-transitory storage medium readable by a processing circuit and storing instructions for execution by the processing circuit for performing a method. The method includes monitoring a plurality of sensors in the adjustable helmet and performing an analysis of play for a user of the adjustable helmet based on data received from the plurality of sensors. The method also includes determining if an adjustment to the adjustable helmet should be made based on the analysis of play and creating an alert indicating that an adjustment to the helmet is needed.

BRIEF DESCRIPTION OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

DETAILED DESCRIPTION

In accordance with exemplary embodiments of the disclosure, methods, systems and computer program products for suggesting adjustments to a helmet based on analysis of play are provided. In exemplary embodiments, the helmet includes one or more sensors and one or more adjustable parameters, such as an adjustable chin strap or adjustable internal or external padding. In exemplary embodiments, the sensors may include one or more of accelerometers, gyroscopes, or the like. In one embodiment, the outputs of the sensors are provided to a processor that performs an analysis of the play of the user based on the movements, and/or actions of the user. In exemplary embodiments, the processor determines one or more adjustments to a protection profile of the helmet are needed based on the analysis of the play of the user. The protection profile of the helmet may include, but is not limited to, the tightness of the chin strap, the size of one or more pads of the helmet, the stiffness of one or more pads of the helmet and the lateral mobility of one or more pads of the helmet. In exemplary embodiments, the protection profile can be determined based on a probability of certain types of impacts occurring and based upon the analysis of the play of the user.

Figure 1:
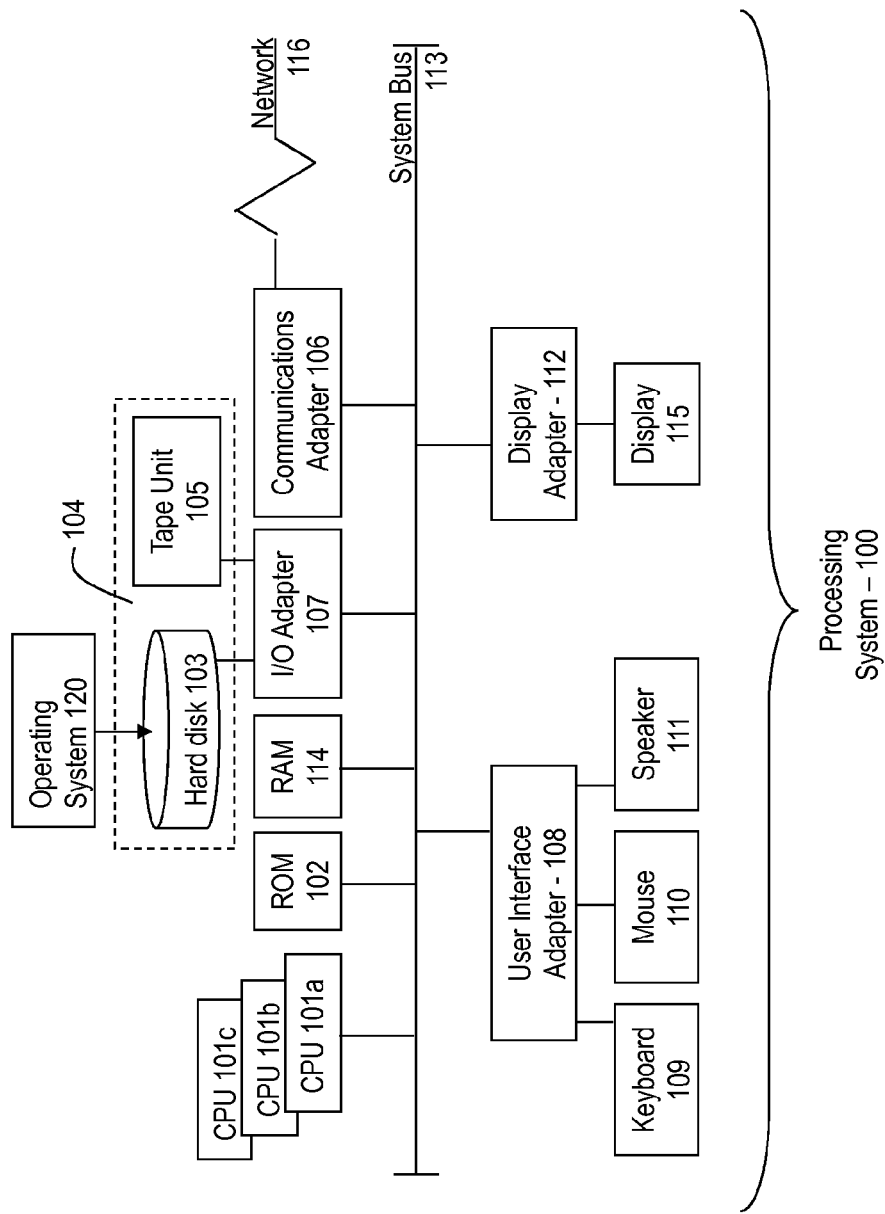
FIG. 1 is a block diagram illustrating one example of a processing system for practice of the teachings herein.

Referring to FIG. 1, there is shown an embodiment of a processing system 100 for implementing the teachings herein. In this embodiment, the system 100 has one or more central processing units (processors) 101a, 101b, 101c, etc. (collectively or generically referred to as processor(s) 101). In one embodiment, each processor 101 may include a reduced instruction set computer (RISC) microprocessor. Processors 101 are coupled to system memory 114 and various other components via a system bus 113. Read only memory (ROM) 102 is coupled to the system bus 113 and may include a basic input/output system (BIOS), which controls certain basic functions of system 100.

FIG. 1 further depicts an input/output (I/O) adapter 107 and a network adapter 106 coupled to the system bus 113. I/O adapter 107 may be a small computer system interface (SCSI) adapter that communicates with a hard disk 103 and/or tape storage drive 105 or any other similar component. I/O adapter 107, hard disk 103, and tape storage device 105 are collectively referred to herein as mass storage 104. Operating system 120 for execution on the processing system 100 may be stored in mass storage 104. A network adapter 106 interconnects bus 113 with an outside network 116 enabling data processing system 100 to communicate with other such systems. A screen (e.g., a display monitor) 115 is connected to system bus 113 by display adaptor 112, which may include a graphics adapter to improve the performance of graphics intensive applications and a video controller. In one embodiment, adapters 107, 106, and 112 may be connected to one or more I/O busses that are connected to system bus 113 via an intermediate bus bridge (not shown). Suitable I/O buses for connecting peripheral devices such as hard disk controllers, network adapters, and graphics adapters typically include common protocols, such as the Peripheral Component Interconnect (PCI). Additional input/output devices are shown as connected to system bus 113 via user interface adapter 108 and display adapter 112. A keyboard 109, mouse 110, and speaker 111 all interconnected to bus 113 via user interface adapter 108, which may include, for example, a Super I/O chip integrating multiple device adapters into a single integrated circuit.

Thus, as configured in FIG. 1, the system 100 includes processing capability in the form of processors 101, storage capability including system memory 114 and mass storage 104, input means such as keyboard 109 and mouse 110, and output capability including speaker 111 and display 115. In one embodiment, a portion of system memory 114 and mass storage 104 collectively store an operating system such as the AIX® operating system from IBM Corporation to coordinate the functions of the various components shown in FIG. 1.

Figure 2:
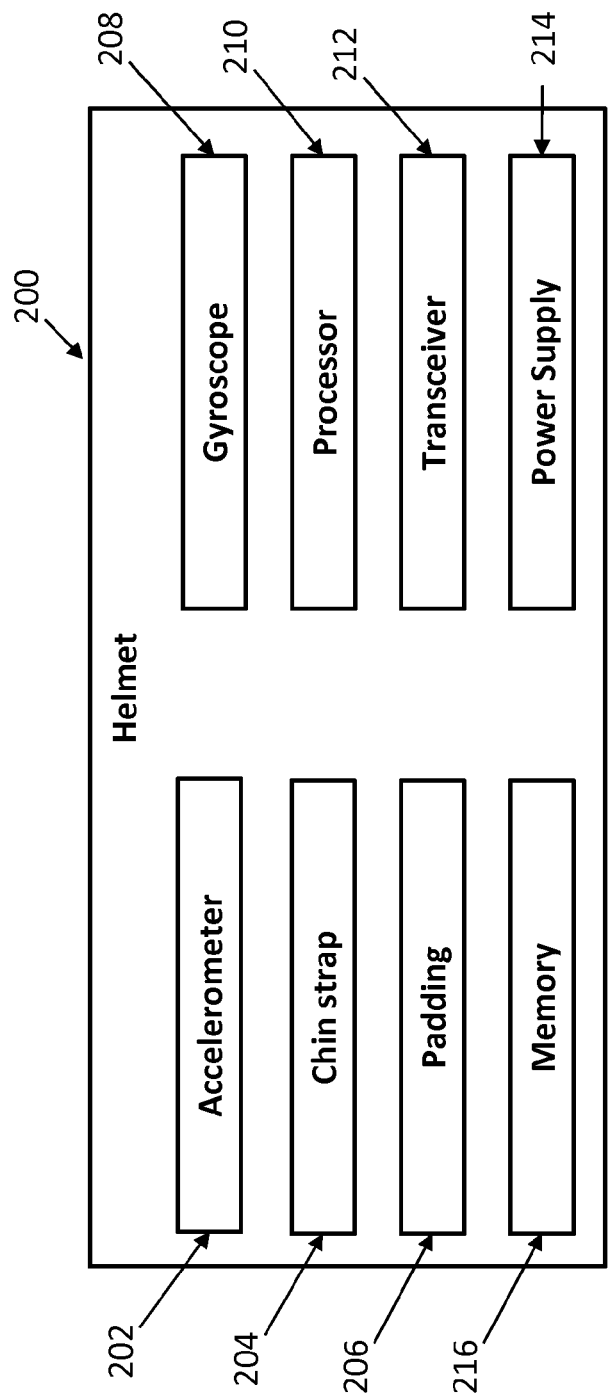
FIG. 2 is a block diagram illustrating an adjustable helmet in accordance with an exemplary embodiment.

Referring now to FIG. 2, a block diagram illustrating an adjustable helmet 200 in accordance with an exemplary embodiment is shown. The term helmet may include, but is not intended to be limited to, a football helmet, a motorcycle helmet or the like. In exemplary embodiments, the adjustable helmet 200 includes one or more of the following an accelerometer 202, a chin strap 204, a padding 206, a gyroscope 208, a processor 210, a transceiver 212, a power supply 214 and a memory 216. In exemplary embodiments, the power supply 214 may be a battery configured to provide power to one or more of the accelerometer 202, the gyroscope 208, the processor 210 and the transceiver 212.

In one embodiment, the processor 210 is configured to receive an output from one or more of the accelerometer 202 and the gyroscope 208 and to perform an analysis of the play of the user of the adjustable helmet. The analysis of the play of the user may include determining a category of play of the user, which is the manner in which the user is using the helmet. In one example, for a football helmet, the category of play may refer to the position being played by the user, running back, wide receiver, linemen, etc. In addition, the analysis of play may include a statistical analysis of the amount of time and characteristics of the activities being performed by the user. For example, the statistical analysis may include analyzing the frequency and intensity of specific movements, i.e., how often a user is running and how fast, how often a user is impacted and how severe are the impacts, etc.

In exemplary embodiments, the padding 206 of the adjustable helmet 200 may include either or both of internal padding or external padding that can have one or more functional parameters adjusted. In one embodiment, the padding 206 may include electroactive polymers that can be used to change the size, shape, and/or stiffness of the padding 206, thereby adjusting the protection profile of the adjustable helmet 200. In another embodiment, the padding 206 may include inflatable padding that can be inflated and deflated to adjust the protection profile of the adjustable helmet 200. In additional embodiments, the padding 206 may be coupled to the helmet by a liner that selectively allows the padding 206 to move laterally in relation to the shell of the helmet. For example, the liner may be configured to allow the padding to slide, or slip, along the surface of the shell of the helmet to reduce the torque on the user's head during an impact. In exemplary embodiments, the degree, or amount of lateral movement, of the liner with respect to the shell may be selected based on the analysis of play of the user of the helmet.

Figure 3:
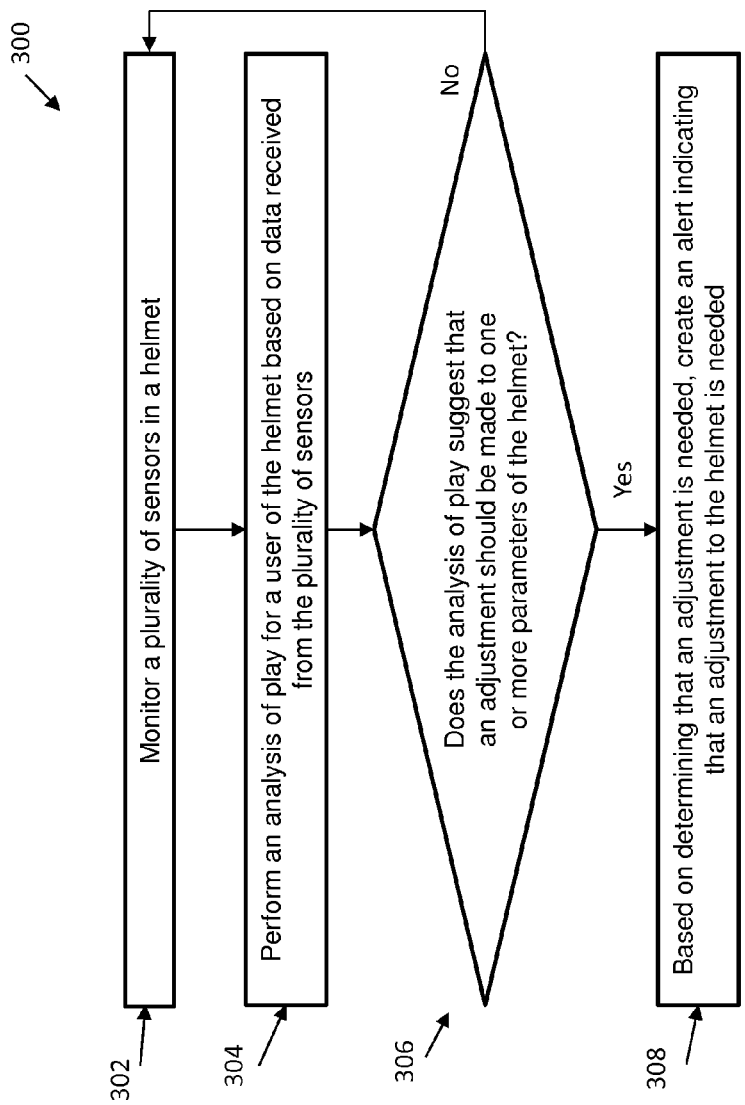
FIG. 3 is a flow diagram of a method for suggesting adjustments to an adjustable helmet based on analysis of play in accordance with an exemplary embodiment.

Referring now to FIG. 3, a flow diagram of a method 300 for suggesting adjustments to an adjustable helmet based on analysis of play in accordance with an exemplary embodiment is shown. As shown at block 302, the method 300 includes monitoring a plurality of sensors in an adjustable helmet. In exemplary embodiments, the plurality of sensors includes one or more of an accelerometer and a gyroscope. Next, as shown at block 304, the method 300 includes performing an analysis of play for a user of the helmet based on data received from the plurality of sensors. In exemplary embodiments, the processor of the adjustable helmet may also be used to create a baseline profile of the play of the user based on input form the accelerometer and the gyroscope and may store the baseline profile in the memory. The processor may compare the readings from the accelerometer and the gyroscope with the stored baseline profile during the analysis of play for a user.

Continuing with reference to FIG. 3, as shown at decision block 306, the method 300 includes determining if an adjustment to one or more parameters of the helmet should be made based on the analysis of play. In exemplary embodiments, the adjustments may include, but are not limited to, adjusting the stiffness on the padding, adjusting the tightness of the chin strap, adjusting the size of the padding, etc. The type and amount of an adjustment may be determined based on a model of expected risks of specific types of impacts given the analysis of play to mitigate the brain injury from these impacts. The adjustments to be made to the helmet may be uniform or non-uniform, i.e., the stiffness of all of the padding may not be the same. For example, based on the analysis of play the stiffness of the padding in the front portion of the helmet may be greater or less that the stiffness in the back of the helmet. Based on a determination that an adjustment to one or more parameters of the helmet should be made, the method proceeds to block 308 and includes creating an alert indicating that an adjustment to the helmet is needed. Based on determining that an adjustment to one or more parameters of the helmet should not be made, the method 300 continues monitoring the plurality of sensors in an adjustable helmet, as shown at block 302.

In one embodiment, the adjustment alert may include a visual alert disposed on the helmet such that the user or other personnel can easily identify the alert. In another embodiment, the method may also include transmitting the alert to a separate processing system. For example, the helmet may transmit an alert to a processing system on a sideline that indicates that an adjustment needs to be made to the helmet. The alert may include an identification of the user, the nature of the adjustment to be made, the amount of the adjustment to be made, and an indication of how critically the adjustment is needed.

Figure 4:
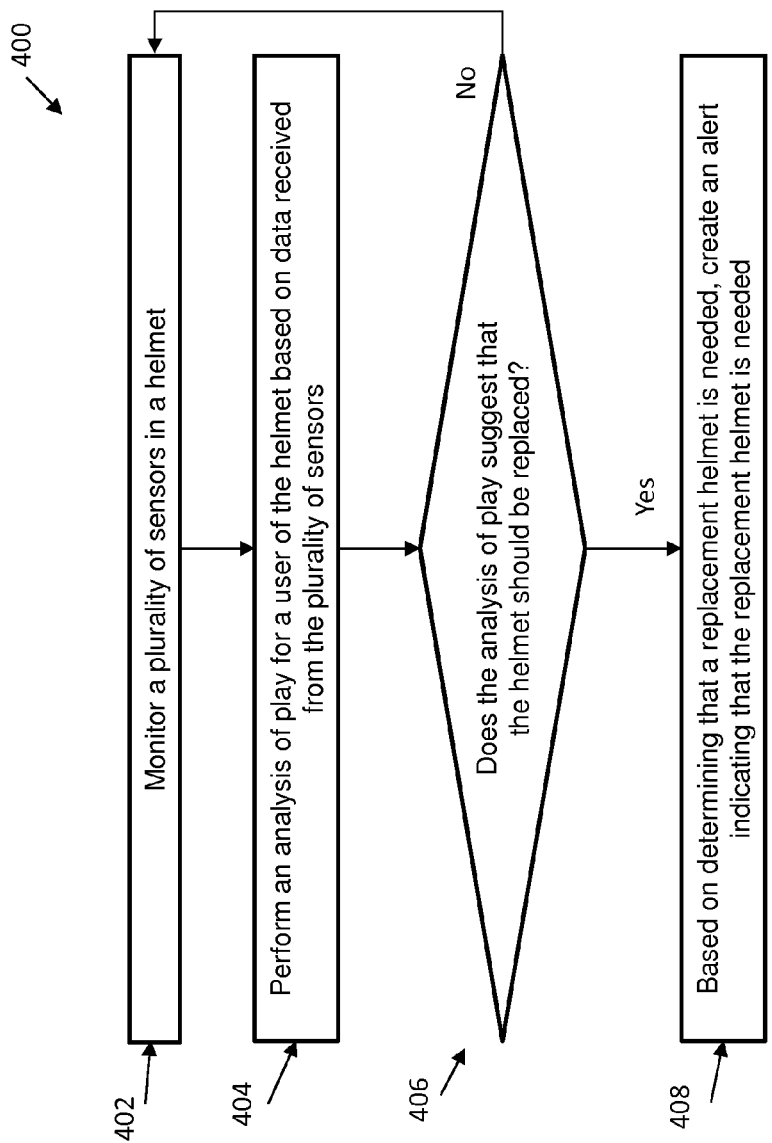
FIG. 4 is a flow diagram of a method for suggesting replacement of a helmet based on analysis of play in accordance with an exemplary embodiment.

Referring now to FIG. 4, a flow diagram of a method 400 for suggesting replacement of a helmet based on analysis of play in accordance with an exemplary embodiment is shown. As shown at block 402, the method 400 includes monitoring a plurality of sensors in an adjustable helmet. In exemplary embodiments, the plurality of sensors includes one or more of an accelerometer and a gyroscope. Next, as shown at block 404, the method 400 includes performing an analysis of play for a user of the helmet based on data received from the plurality of sensors. As shown at decision block 406, the method 400 also includes determining if the helmet should be replaced based on the analysis of the play of the user. In exemplary embodiments, the determination that the helmet should be replaced may be triggered by an indication that a portion of the helmet has failed or is failing, that a needed adjustment is beyond the range of available adjustments in the current helmet, or that a different helmet has a protection profile more suited to the play of the user. Based on a determination that the helmet should be replaced, the method proceeds to block 408 and includes creating an alert indicating that a replacement helmet is needed. Based on determining that the helmet does not need to be replaced, the method 400 continues monitoring the plurality of sensors in an adjustable helmet, as shown at block 402.

In one embodiment, the replacement alert may include a visual alert disposed on the helmet such that the user or other personnel can easily identify the alert. In exemplary embodiments, the replacement alert may be different than an adjustment alert. For example, the different types of alerts may be different color LEDs on the helmet. In another embodiment, the method may also include transmitting the alert to a separate processing system. For example, the helmet may transmit an alert to a processing system on a sideline that indicates that the helmet needs to be replaced. The alert may include an identification of the user, the cause of the replacement, an indication of a type of a replacement helmet, and an indication of how critically the replacement is needed.

In exemplary embodiments, the analysis of the play of the user can include monitoring data for an angle of rotation during an impact and comparing it to a stored preferred angle of rotation during an impact. Likewise, the analysis of the play of the user can include monitoring data for helmet acceleration during impacts using this data in functions to track the wear and tear of the adjustable helmet. In addition, the data for helmet acceleration may be analyzed and correlated with onboard chin strap tension estimator functions. In exemplary embodiments, if during the analysis any of the monitored data or combinations of the monitored data exceeds predefined criterion levels, a helmet amelioration action, such as an adjustment or replacement can be requested.

In exemplary embodiments, the analysis of play by the adjustable helmet can be configured to detect excessive wear and tear on the helmet, an incorrect chin strap adjustment during use, an incorrect fit of the helmet on the user, and the like. In addition, the helmet adjustments that can be made may make helmet better at dealing with a certain angle of rotation over others by changes to angular rotation damping mechanisms in the coupling of helmet to head.

Figure 5:
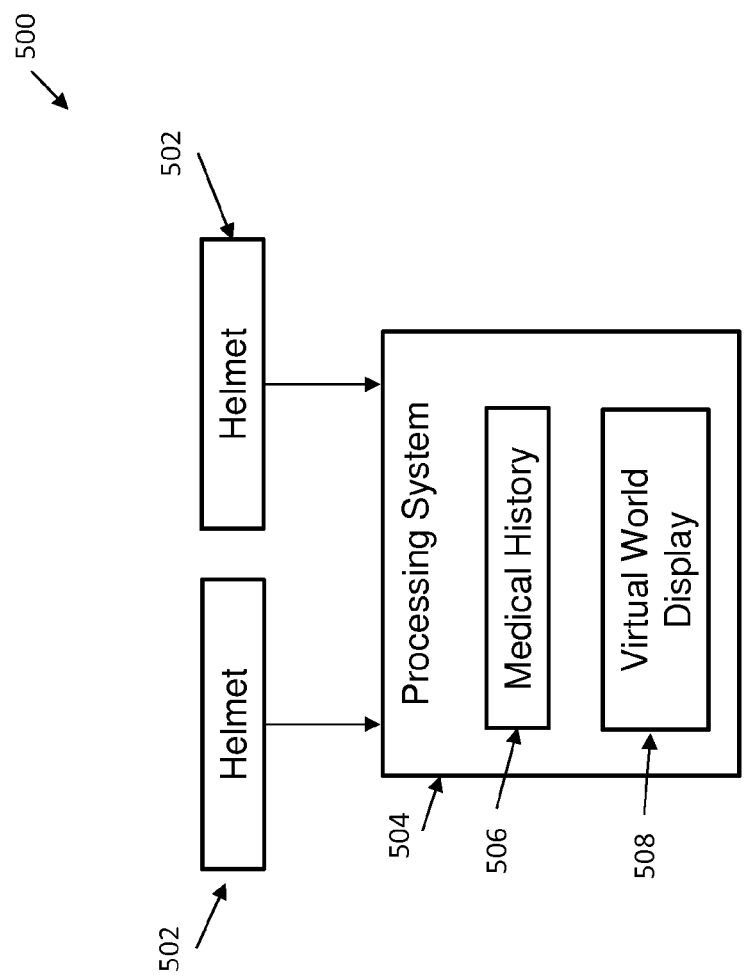
FIG. 5 is a block diagram illustrating a system for monitoring adjustable helmets in accordance with an exemplary embodiment.

Referring now to FIG. 5, a block diagram illustrating a system 500 for monitoring adjustable helmets in accordance with an exemplary embodiment is shown. As illustrated the system 500 includes one or more adjustable helmets 502, such as the one shown and described above with reference to FIG. 2, and a processing system 504, such as the one shown and described above with reference to FIG. 1. The processing system 504 is configured to communicate with the helmets 502 and is also configured to store the medical history 506 of the users of the helmets 502. In exemplary embodiments, the medical history 506 of the users of the helmets 502 may be used by the helmet in determining what adjustments need to be made to the helmet during play. In addition, the processing system 504 may include a virtual world display 508 that is configured to provide a display a real-time status of each of the users of the helmets. In exemplary embodiments, the status may include, if a replacement or adjustment is needed to a helmet, a category of play of each user, any indications that the user may have suffered a traumatic brain injury, a duration of play of the user, a duration that the user has been in the current category of play, or the like.

In exemplary embodiments, the user's history of collision or medical concerns may be used to determine a traumatic brain injury risk assessment, either by the embedded processor or the separate processing system. In addition, the helmet may be configured to provide a real-time feed of the user's cognitive state to increase the confidence level of the need for an adjustment to the helmet. In exemplary embodiments, an aggregate indication may be used to summarize an overall state of a group of players. This may also help to potentially identify area of risk in the dynamics of player-player interaction, overly aggressive players, playing field conditions, etc. In exemplary embodiments, an automatic feed from a user's history of collision or medical concerns may also be provided to a processor of the helmet in order to update an impact risk model for each category of play. In addition, the processing system 504 may receive a real-time feed of the user's cognitive state, which can be used to update the risk models used by the helmets. The risk models may also be sent to the virtual world display 508 of the game and players, which allows the sports staff health professionals to visualize the nature of potential problems.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A computer program product for automatic adjustment of helmet parameters based on a category of play, the computer program product comprising:
   a non-transitory storage medium readable by a processing circuit and storing instructions for execution by the processing circuit for performing a method comprising:
   monitoring a plurality of sensors in the adjustable helmet;
   performing an analysis of play for a user of the adjustable helmet based on data received from the plurality of sensors;
   determining if an adjustment to a protection profile of the adjustable helmet should be made based on the analysis of play, wherein the protection profile includes a stiffness of at least one pad of the adjustable helmet, a size of at least one pad of the helmet and a tightness of a chin strap of the helmet; and
   creating an alert indicating that the adjustment to the helmet is needed, wherein the alert includes an identification of the user, a type of the adjustment, an amount of the adjustment and an indication of how critically the adjustment is needed.

2. The computer program product of claim 1, wherein the alert is a visual alert disposed on the adjustable helmet.

3. The computer program product of claim 2, wherein the alert includes one of an adjustment alert and a replacement alert.

4. The computer program product of claim 1, further comprising transmitting the alert to a separate processing system.

5. The computer program product of claim 1, wherein the determination that the adjustment to the adjustable helmet should be made is further based on a risk profile associated with a medical history of the user.

6. The computer program product of claim 5, wherein the risk profile is further based on a category of play of the user.

7. An adjustable helmet for mitigating the risk of brain comprising:
 a processor and one or more sensors, the processor configured for performing a method comprising:
 monitoring the one or more sensors in the adjustable helmet;
 performing an analysis of play for a user of the adjustable helmet based on data received from the one or more of sensors;
 determining if an adjustment to a protection profile of the adjustable helmet should be made based on the analysis of play, wherein the protection profile includes a stiffness of at least one pad of the adjustable helmet, a size of at least one pad of the helmet and a tightness of a chin strap of the helmet; and
 creating an alert indicating that the adjustment to the helmet is needed, wherein the alert includes an identification of the user, a type of the adjustment, an amount of the adjustment and an indication of how critically the adjustment is needed.

8. The adjustable helmet of claim 7, wherein the alert is a visual alert disposed on the adjustable helmet.

9. The adjustable helmet of claim 8, wherein the alert includes one of an adjustment alert and a replacement alert.

10. The adjustable helmet of claim 7, wherein the determination that the adjustment to the adjustable helmet should be made is further based on a risk profile associated with a medical history of the user.

11. The adjustable helmet of claim 10, wherein the risk profile is further based on a category of play of the user.

* * * * *